United States Patent [19]

Patrascu et al.

[11] Patent Number: 5,288,926
[45] Date of Patent: Feb. 22, 1994

[54] PROCESS FOR PREPARING A BISPHENOL

[75] Inventors: Emil Patrascu, Stade; Dieter Tank, Himmelpforten; Jochen Gressmann; Johann-Wilhelm Frey, both of Stade; Ulrich Wallbaum, Fredenbeck, all of Fed. Rep. of Germany

[73] Assignee: The Dow Chemical Company, Midland, Mich.

[21] Appl. No.: 13,603

[22] Filed: Feb. 4, 1993

[30] Foreign Application Priority Data

Mar. 2, 1992 [GB] United Kingdom ............... 9204490

[51] Int. Cl.$^5$ .............................................. C07C 39/16
[52] U.S. Cl. ................................... 568/727; 568/722; 568/723; 568/724
[58] Field of Search ............... 568/722, 727, 723, 728, 568/724

[56] References Cited

U.S. PATENT DOCUMENTS

| | | | |
|---|---|---|---|
| 3,049,569 | 8/1972 | Apel et al. | 568/727 |
| 4,107,218 | 8/1978 | Konrad et al. | 568/724 |
| 4,191,843 | 5/1980 | Kwantes et al. | 568/727 |
| 4,354,046 | 10/1982 | Ladewig et al. | 568/724 |
| 4,740,635 | 1/1988 | Gomes de Matos et al. | 568/724 |
| 4,766,254 | 8/1988 | Faler et al. | 568/724 |
| 4,861,919 | 8/1989 | Robbins et al. | 568/724 |

FOREIGN PATENT DOCUMENTS

| | | | |
|---|---|---|---|
| 0001863 | 3/1978 | European Pat. Off. | 568/724 |
| 0265792 | 10/1987 | European Pat. Off. | 568/724 |
| 4014992 | 11/1991 | Fed. Rep. of Germany | 568/727 |

Primary Examiner—Werren B. Lone

[57] ABSTRACT

Bisphenols are prepared by
a) reacting a phenolic compound with a carbonyl compound in a reaction mixture, containing the carbonyl compound, a stoichiometric excess of the phenolic compound and a catalyst, to produce a product mixture containing a bisphenol,
b) separating bisphenol from the product mixture to leave a mother liquor and
c) recycling at least a portion of the mother liquor to the reaction mixture.

At least a portion of the phenolic compound is contacted with a strongly acidic cation exchange resin and a strongly basic anion exchange resin before the phenolic compound is used in the reaction step a) and/or at least a portion of the product mixture and/or at least a portion or the mother liquor is contacted with a strongly acidic cation exchange resin and a strongly basic anion exchange resin before mother liquor is recycled to the reaction mixture.

19 Claims, No Drawings

PROCESS FOR PREPARING A BISPHENOL

BACKGROUND OF THE INVENTION

The present invention relates to the preparation of bisphenol of improved purity. Bisphenols are used as a starting material for the preparation of various materials, notably epoxy resins and polycarbonates. Bisphenols are usually prepared by the condensation reaction of an aldehyde or a ketone and a stoichiometric excess of a phenol in a reaction mixture in the presence of a catalyst. The product mixture is usually passed to a crystallization zone wherein a crystalline bisphenol product and a mother liquor recycle stream is produced. The mother liquor contains a major amount of a phenol and is usually recycled to the reaction mixture. However, this condensation reaction using any known catalyst always produces a number of by-products. The product mixture contains, in addition to the desired bisphenol, excess phenol, catalyst, unreacted aldehyde or ketone, water, a variety of by-products, such as 2-(2-hydroxyphenyl)-2-(4-hydroxyphenyl)propane (hereafter referred to as o,p'-bisphenol isomer), 2,2,4-trimethyl-4-(4-hydroxyphenyl)chroman, trisphenol, polyphenol and unfavorably colored substances. A portion of these by-products in the product mixture originates from the recycled mother liquor. The repeated recycling of the mother liquor typically results in a build-up of by-products in the product mixture. These by-products have an unfavorable influence on the quality of the resins prepared from the bisphenols. It is well known that the production of polycarbonates requires a bisphenol of very high purity.

Accordingly, many suggestions have been made to increase the purity of bisphenols, such as bisphenol A (2,2'-bis(4-hydroxyphenyl)-propane), either by separating the by-products from the bisphenol in the product mixture or by purifying the mother liquor to be recycled in order to decrease the concentration of the by-products in the product mixture.

U.S. Pt. No. 4,354,046 relates to process of purifying bisphenol A wherein unreacted phenol, acetone and water is removed from the crude reaction mixture and the remaining crude bisphenol A is mixed with water and toluene. This mixture is heated to form a single liquid phase. The liquid phase is then cooled whereby bisphenol A crystallizes. The remaining liquor is distilled to remove water and toluene. Phenol is added to the remainder. This mixture contains large amounts of the o,p'-isomer of bisphenol A and other by-products. The mixture is passed through a bed of cation exchange resin in acid form to convert most of the by-products to the desired bisphenol A. The effluent from the cation exchange bed can be recycled to the bisphenol reactor.

U.S. Pat. No. 4,107,218 relates to a process of reducing the content of color bodies in the bisphenol A recycle stream. After the separation of the product mixture obtained in the bisphenol A process into a bisphenol A/phenol adduct and a mother liquor recycle stream; the recycle stream is contacted with an acidic cation exchange resin to reduce the content of color bodies contained in the mother liquor stream. The acidic cation exchange resin is periodically reactivated by washing with a phenol/water mixture.

U.S. Pat. No. 4,766,254 teaches that product losses and color formation are sometimes encountered when bisphenol A is produced from phenol and acetone in the presence of a cation exchange resin (which is used as a catalyst). It is taught that the product stream from the reaction is frequently separated into a solid adduct of bisphenol A and phenol and a liquid stream which contains crude bisphenol A and various impurities from which further bisphenol A is recovered by distillation. The U.S. patent further teaches that sometimes substantial product losses occur during this distillation step and that the mother liquor is frequently contaminated with darkly colored materials which are difficult or impossible to remove during bisphenol A purification. In order to suppress such losses and to decolorize the liquid stream which contains crude bisphenol A, the U.S. patent suggests to remove acid impurities from the crude liquid stream by contact with a basic ion exchange resin before further bisphenol A is recovered from the resin-treated crude liquid stream by distillation.

U.S. Pat. No. 4,191,843 teaches a process of producing bisphenols by reacting at least two moles of phenol with acetone in a reaction zone in the presence of an acid ion exchanger, such as a sulfonated ion-exchange resin. The reaction zone effluent is contacted with an acid ion exchanger in metal salt form and/or a weak base ion exchanger. The U.S. patent teaches that the reaction zone effluent is preferably first contacted with an strong-acid ion exchanger before it is contacted with an acid ion exchanger in metal salt form and/or a weak base ion exchanger. After the reaction zone effluent has been contacted with the acid ion exchanger in metal salt form and/or the weak base ion exchanger, water and acetone are removed from the reaction zone effluent and the bisphenol is recovered from the residue of the separation.

German Offenlegungsschrift DE-A-4014992 relates to the production of bisphenols by reaction of a phenol with an aldehyde or ketone. Crude phenol is utilized, which originates from the working up of carbonaceous products, such as brown coal or waste from the hydration of coal or from the working up of waste waters of crackers. Such crude phenol is first activated with a cation exchange resin in acidic form before it is reacted with an aldehyde or ketone in the presence of a sulfonated cation exchanger in acidic form. The resulting reaction mixture is treated with an anion exchanger of weak or average basicity.

Although the purity of the produced bisphenols is considerably improved by the taught processes, their purity is sometimes still not sufficient, especially if the bisphenols are intended to be used for producing polycarbonates. Accordingly, it is still desirable to provide an improved process by which bisphenols can be produced at high purity.

SUMMARY OF THE INVENTION

One aspect of the present invention relates to a process of preparing a bisphenol which comprises the steps of a) reacting a phenolic compound with a carbonyl compound in a reaction mixture, containing the carbonyl compound, a stoichiometric excess of the phenolic compound and a catalyst, to produce a product mixture containing a bisphenol, b) separating bisphenol from the product mixture to leave a mother liquor and c) recycling at least a portion of the mother liquor to the reaction mixture.

The process is characterized in that i) at least a portion of the phenolic compound is contacted with a strongly acidic cation exchange resin and a strongly basic anion exchange resin before the phenolic compound is used in the reaction step a) and/or ii) at least a portion of the product mixture and/or at least a portion or the mother liquor is contacted with a strongly acidic cation exchange resin and a strongly basic anion exchange resin before mother liquor is recycled to the reaction mixture.

Another aspect of the present invention relates to a bisphenol A which has been produced according to the process of the present invention.

Surprisingly, it has been found that the purification is considerably more effective when product mixture, mother liquor and/or phenolic compound is contacted with a strongly acidic cation exchange resin and a strongly basic anion exchange resin than when product mixture or mother liquor is contacted with an ion exchange resin as suggested in the prior art, i.e. a) with an acidic cation exchange resin alone (U.S. Pat. Nos. 4,107,218 and 4,354,046) or b) with an anion exchange resin alone (U.S. Pat. No. 4,766,254) or c) first with a strong-acid ion exchange resin and then with a weak basic ion exchange resin (U.S. Pat. No. 4,191,843).

DETAILED DESCRIPTION OF THE INVENTION

Step a) of the process of the present invention, that is the reaction of a phenolic compound with a carbonyl compound in a reaction mixture which contains the carbonyl compound, a stoichiometric excess of the phenolic compound and a catalyst, is generally well known in the art. The process is described in general in U.S. Pat. Nos. 3,049,569 and 4,107,218 and in the references cited therein. More than 2 moles of phenolic compound per mole of carbonyl compound are present in the reaction mixture. The molar ratio between phenolic compound and carbonyl compound preferably is between 2:1 and 45:1, more preferably from 6:1 to 16:1.

The phenolic compound employed as the starting material in the production of bisphenols can be any compound containing hydroxyl group linked to a carbon of the aromatic group. Suitable phenolic compounds include, for example, phenols and substituted phenols, such as: phenol, cresols, xylenols, chlorophenols, thymol, carvacrol, cumenol, 2-methyl-6-ethylphenol, 2,4-dimethyl-3-ethylphenol, 4-ethylphenol, 2-ethyl-4-methylphenol, 2,3,6-trimethylphenol, 2-methyl-4-tertiary-butylphenol, 2,4-ditertiary-butyl-phenol, 4-methyl-2-tertiary-butylphenol, 2-teritary-butyl-4-methylphenol, 2,3,5,6-tetramethylphenols, 2,6-dimethylphenol, 2,6-ditertiary-butylphenol, 3,5-dimethylphenol, 3,5-diethylphenol, 2-methyl-3,5-diethylphenol, o-phenylphenol, p-phenylphenol, tetraphenolethane, the naphthols, phenanthrol, their homologues and analogues. Suitable phenolic compounds include those containing one or more phenolic group in each nucleus as well as polynuclear compounds.

The carbonyl compound employed as the starting material can be any compound of the following formula:

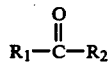

wherein $R_1$ represents a member of the group consisting of any aliphatic, cycloaliphatic, aromatic and heterocyclic radicals, and $R_2$ represents a member of the group consisting of hydrogen, aliphatic, cycloaliphatic, aromatic and heterocyclic radicals. Suitable carbonyl compounds include ketones and aldehydes. Examples of suitable ketones include, for example, acetone, 1,3-dichloroacetone, dimethyl ketone, methyl ethyl ketone, diethyl ketone, dibutyl ketone, methyl isobutyl ketone, cyclohexanone, fluorenone, preferably 9-fluorenone, propionylphenone, methyl amyl ketone, mesityl oxide, cyclopentanone, acetophenone, and examples of suitable aldehydes include formaldehyde, acetaldehyde, propionaldehyde, butyraldehyde and benzaldehyde.

The specific phenolic compound and carbonyl compound employed as starting material will depend upon the specific bisphenol compound desired and may be governed to some extent by specific operating conditions employed. The invention process is particularly suitable for production of bisphenol-A, for which the carbonyl compound is acetone and the phenolic compound is phenol.

It has been found that commercially available phenolic compounds, such as phenol, often contain small amounts of by-products, such as organic and/or inorganic acids or salts. Although the amount of these by-products is typically less than 250 weight ppm, the activity an acidic ion exchange resin which is used as a catalyst in the reaction between the phenolic compound and the carbonyl compound is affected. The cations of the salt-type by-products are retained in the catalyst whereby its activity is reduced. Furthermore, the reaction mixture is enriched in free acid. It has been found to be very advantageous to subject a portion or the entire amount of the phenolic starting material with a strongly acidic cation exchange resin and a strongly basic anion exchange resin before the phenolic compound is reacted with the carbonyl compound. The preferred types of strongly acidic cation and strongly basic anion exchange resins are the same as the ones described further below with reference to the treatment of product mixture. The phenolic starting material preferably is contacted with a strongly acidic cation exchange resin and a strongly basic anion exchange resin at a temperature of from 40°–120° C., preferably from 40° to 95° C., more preferably of from 45° to 70° C. The speed of the phenolic compound through one or more beds containing the strongly acidic cation exchange resin and the strongly basic anion exchange resin, expressed as weight hourly space velocity (WHSV) preferably is from 0.5 to 24 hrs$^{-1}$, more preferably from 2 to 14 hrs$^{-1}$. If the phenolic compound is passed through a strongly acidic cation exchange resin and a strongly basic anion exchange resin, preferably from 20 to 100%, more preferably from 50 to 100%, most preferably from 90 to 100%, of the entire volume of the phenolic compound is passed through these resins. The treatment of phenol with a strongly acidic cation exchange resin and a strongly basic anion exchange resin results in a highly purified, stabilized and decolorized phenol.

The phenolic compound and the carbonyl compound are preferably reacted at a temperature of from 40° to 120° C., preferably from 45° to 85° C. The reaction can be carried out at atmospheric, sub-atmospheric or superatmospheric pressure. Any known catalyst is useful, however strong acid ion exchange resins are preferred. Preferred ion exchange resins contain sulfonic acid groups. Exemplary thereof are sulfonated styrenedivinylbenzene copolymers, sulfonated cross-linked styrene polymers, phenol formaldehyde sulfonic acid resins and benzene-formaldehyde-sulfonic acid resins. These strong acid ion exchange resins are advantageously used in combination with a mercaptan as a reaction rate accelerator. The most preferred catalysts are promoted, sulfonated polystyrene resins. The resins may for example be promoted by treating the resins with a mercapto alcohol prior to their use as described in column 5 of U.S. Pat. No. 3,049,569. Other useful promoters are $HS-CH_2-CH_2-NH_2$ or $(HS-CH_2-CH_2-)_2NH$. To initiate the reaction, the phenolic compound and the carbonyl compound are advantageously heated to the reaction temperature and passed into a fixed bed of the ion exchange resin, preferably downward, at a slight pressure to maintain an adequate rate of flow through the bed, although gravity flow through the column is equally satisfactory.

The obtained reaction mixture contains bisphenol, the non-reacted phenolic compound, usually some non-reacted carbonyl compound, water and by-products. Preferably, water and the carbonyl compound are removed from the obtained product mixture by evaporation in a dehydrator. Depending upon the temperature of the product mixture, the mixture may be heated or cooled in order to cause evaporation of water of reaction and non-reacted carbonyl compound. A minor amount of phenolic compound might also be evaporated. The evaporated mixture of carbonyl compound, water and optionally phenolic compound may be passed into a dehydrator for removal of water, leaving the carbonyl compound and the phenolic compound which are advantageously recycled to the process. The temperature in the dehydrator preferably is from 45° to 220° C., more preferably from 60° to 170° C. The pressure in the dehydrator preferably is from 10 to 700 mbar, more preferably from 80 to 350 mbar. The evaporation of the mixture of water, carbonyl compound and phenolic compound and the dehydration of this mixture are preferably carried out as described in detail in U.S. Pat. No. 3,049,569.

After removal of water, carbonyl compound and optionally a minor amount of phenolic compound, bisphenol is separated from the product mixture, usually in a crystallizer, to leave a mother liquor stream. Before or after removal of water, carbonyl compound and optionally phenolic compound and prior to the separation of bisphenol from the product mixture, the product mixture or a portion thereof may be contacted with a strongly acidic cation exchange resin and a strongly basic anion exchange resin. Before product mixture is contacted with these ion exchange resins, it may be subjected to an isomerization step by means of a cation exchanger, such as described in U.S. Pat. Nos. 4,375,567 and 4,882,923., Any known strongly acidic cation exchange resin and strongly basic anion exchange resin may be used in the process of the present invention. The terms "strongly acidic cation exchange resin" and "strongly basic anion exchange resin" and examples of such resins are known in the Art, see for example "Ullmann's Enzyklopaedie der Technischen Chemie", 4th Edition, Vol. 13, page 297 etc. The ion exchange resins usually are in the form of beads. Ion exchange resins have a polymeric matrix and functional ion exchange exchange groups.

Various cross-linked polymers are useful as a matrix for the resin beads. One known type of matrix is based on phenol/formaldehyde condensation polymers which are cross-linked with an aldehyde, a chlorinated hydrocarbon or an epoxy compound. Other known types of matrixes are cross-linked polymers of vinylbenzyl chloride, of acrylic acid or of acrylamide or a polyacrylate. The preferred matrixes are cross-linked polystyrene or cross-linked poly(alpha-methylstyrene) or a cross-linked polymer of styrene or alpha-methylstyrene which is substituted at the benzene ring with $C_{1-6}$-alkyl, for example methyl, ethyl, tert. butyl, isopropyl, or a halogeno-$C_{1-6}$-alkyl, e.g. chloromethyl, or aminomethyl. The cross-linking agent preferably is an alkyl acrylate or a di- or polyvinyl compound such as trivinyl cyclohexane, ethylene glycol dimethacrylate or trimethylolpropane triacrylate, most preferably divinylbenzene or trivinylbenzene. Divinylbenzene is typically copolymerized with the substituted or unsubstituted styrene or with acrylic acid.

Preferred ion exchange resins beads which are used in the process of the present invention have a cross-linked styrene-divinylbenzene copolymer matrix.

The resin beads can have a macroporous or gel type (microporous) structure. The macroporous resin beads preferably have an average pore diameter of more than 10 nm. The microporous resin beads preferably have an average pore diameter of 0.5 to 5 nm. These resin beads may be prepared according to conventional suspension polymerization techniques such as those taught in U.S. Pat. Nos. 4,564,644, 4,297,220 and 4,382,124.

Preferred resin beads are cross-linked spheroid copolymer beads which have a core/shell morphology. By the term "core/shell morphology" it is meant that the polymeric structure of the copolymer beads changes from the inside to the outside of the bead. Such changes in polymeric structure may be somewhat gradual yielding a bead having a gradient of polymeric structure along the radius. Alternatively, said changes in polymeric structure may be relatively abrupt as one moves along a radius of the bead outward from the center. The effect in any case is that these resin beads have a relatively distinct core having one polymeric structure and a relatively distinct shell having another polymeric structure. The core/shell morphology of the copolymer beads is detectable using known analytical techniques such as those mentioned in European patent application 0 101 943. The core/shell copolymer beads preferably have a decreased level of cross-linkages in the shell area as compared to the core area. Usually they have a shell containing a lower proportion of cross-linking monomers than the core. In this way, beads of this type will have a shell which is softer (less friable and more elastic) than the core of the bead. This permits the bead to distribute energy throughout its structure when subjected to external stresses and pressures while retaining its shape and integrity. It is believed that this improves the crush strength and resistance to osmotic shock of such core/shell copolymer beads. In addition to the difference in cross-link densities of the core and shell, the polymer in the shell can advantageously have a higher molecular weight than the polymers of the core. This also can impart mechanical strength to the bead and increase its resistance to osmotic shock. Accordingly, the breakage of the beads is reduced. The core/shell copolymer beads which are useful for preparing acidic cation exchange resin beads and basic anion exchange resin beads are described in detail in European patent application 0 101 943. The resin beads which have a core/shell morphology can have a macroporous or microporous structure as defined above.

The resins are generally used in the shape of beads in their commercially available form. Typically, they have an average diameter of from 0.050 to 1.50 mm, preferably of from 0.10 to 1.20 mm, more preferably of from 0.25 to 0.80 mm.

The functional groups can be directly or indirectly bound to the polymeric matrix. For example the functional groups can be bound to the polymeric matrix via alkylene groups such as $C_{1-3}$-alkylene groups, preferably ethylene or methylene with methylene being the most preferred group.

Functional groups of strongly acidic cation exchange resins typically are —$SO_3H$ or —$PO_3R_1R_2$ groups wherein $R_1$ is hydrogen, a $C_{1-6}$-alkyl, such as a methyl, ethyl, n-propyl, isopropyl, n-butyl, isobutyl, the pentyl or hexyl groups, a $C_{3-6}$-cycloalkyl, such as cyclohexyl, aryl, such as phenyl or benzyl and $R_2$ is hydrogen. A minor portion of the hydrogen ions in the strongly acidic cation exchange groups may be replaced by cations, preferably alkali metal cations, such as sodium or potassium ions. However, it is important that the major portion of the functional groups of the cation exchange resin is in their free acid form instead of in a salt form in order to achieve sufficient purification. Generally more than 70%, preferably more than 80% and most preferably more than 90% of the ion exchange groups should be present in their acidic form. The most preferred functional group is —$SO_3H$. Blends of different strongly acidic cation exchange resins are also useful.

Typically, strongly basic anion exchange resins contain quaternary ammonium groups which are bound to a polymeric matrix and exchangeable anions. Such anions are for example hydroxy, a halogen ion, such as chloride, bromide or iodide; sulfate, nitrate, carbonate or hydrogen carbonate anions. However, it is important that the major portion of the functional groups of the anion exchange resin is in their free base form instead of a salt form in order to achieve sufficient purification. Generally more than 70%, preferably more than 80% and most perferably more than 90% of the ion exchange groups should be present in their free base form, i.e. should contain hydroxy as an exchangeable anion. Functional groups of strongly basic anion exchange resins preferably are

$$-\overset{+}{N}R_3R_4R_5 X^- \text{ groups} \quad (I)$$

wherein $R_3$ and $R_4$ independently in each occurrence are hydrogen or $C_{1-6}$-alkyl such as n-butyl, tert. butyl, sec. butyl, the pentyl groups, the hexyl groups such as n-hexyl, preferably $C_{1-3}$-alkyl, such as methyl, ethyl, n-propyl or isopropyl, $R_5$ is hydrogen, $C_{1-6}$-alkyl, for example those mentioned above, aryl, such as benzyl, or hydroxy-$C_{1-3}$-alkyl, such as hydroxymethylene or hydroxypropylene, preferably hydroxyethylene, Or a mono- or di-Cl-6alkylaminoethylene group, preferably a mono- or di-$C_{1-3}$-alkylaminoethylene group such as dimethyl-, diethyl- or dipropylaminoethylene and X is an anion, preferably hydroxy, a halogen ion, such as chloride, bromine or iodide; or the nitrate, carbonate, hydrogen carbonate or sulfate ion.

The major portion of X is hydroxy, as indicated above. The most preferred functional groups are -NR3R4R5OH groups.

Of the quaternary ammonium groups being bound to the polymeric matrix, trimethylammonium, dimethylbenzylammonium and dimethyl-hydroxyethylene ammonium groups are preferred of which the trimethyl ammonium group is more preferred.

Blends of different strongly basic anion exchange resins are also useful.

The acidic and basic functional groups can be bound to the polymeric matrix via alkylene groups such as Cl-3-alkylene groups, preferably ethylene or methylene with methylene being the most preferred group.

The strongly acidic cation exchange resin and the strongly basic anion exchange resin can be arranged in separate beds or in the same bed. It is not critical whether phenolic compound, product mixture and/or mother liquor is first contacted with the strongly acidic cation exchange resin and then with the strongly basic anion exchange resin or vice versa, however the liquid(s) must be contacted with both types of resins. Preferably, the strongly acidic cation exchange resin and the strongly basic anion exchange resin are arranged in a mixed bed. Such a mixed bed can be produced in a known manner. Several portions of the strongly acidic cation and the strongly basic anion exchange resin may be alternatingly filled into a container, preferably a column. If the strongly acidic cation and the strongly basic anion exchange resin are alternatingly filled into the column, the column contains at least one, preferably at least five and more preferably at least ten portions of strongly acidic cation exchange resin and at least one, preferably at least five and more preferably at least ten portions of strongly basic anion exchange resin which have alternatingly been filled into the container. As used herein, such a bed of alternating layers of strongly acidic cation and strongly basic anion exchange resin is also covered by the definition "mixed bed". When a liquid stream to be purified, such as at least a portion of phenolic compound and/or product mixture and/or mother liquor, is passed through such a mixed bed containing alternating layers of strongly acidic cation and strongly basic anion exchange resins, it is not essential whether the liquid stream contacts first a layer of strongly acidic cation exchange resin or first a layer of strongly basic anion exchange resin. However, it is preferred to blend the strongly acidic cation and the strongly basic anion exchange resin before filling them into the container. The strongly acidic cation and the strongly basic anion exchange resin may be mixed in their dry or water-wet form or as a slurry in water. The mixed bed of a strongly acidic cation and a strongly basic anion exchange resin preferably contains from 15 to 90, more preferably from 50 to 70, weight percent of a strongly acidic cation exchange resin and from 85 to 10, more preferably from 50 to 30, weight percent of a strongly basic anion exchange resin.

Both indicated types of ion exchange resins are suitably fixed and usually supported on one or more grids. Advantageously, the liquid stream to be purified, such as at least a portion of phenolic compound and/or product mixture and/or mother liquor, is passed by the strongly acidic cation exchange resin and the strongly basic anion exchange resin, preferably downward, at a slight pressure to maintain an adequate rate of flow through the bed or beds containing the resins, although gravity flow is equally satisfactory. Alternatively, the liquid stream may be passed upward by the indicated resins.

The useful temperature for contacting the product mixture with a strongly acidic cation exchange resin and a strongly basic anion exchange resin depends on various factors, such as the specific composition of the product mixture, the temperature resistance of the ion exchange resins etc. In any event, the temperature should be high enough that no significant amounts of bisphenol precipitate prior to or during the contact of the product mixture with the resins. The product mixture preferably is contacted with a strongly acidic cation exchange resin and a strongly basic anion exchange resin at a temperature of from 40 to 120° C, preferably from 40° to 95° C., more preferably of from 45° to 70° C. The speed of the product mixture through one or more beds containing the resins, expressed as weight hourly space velocity (WHSV) preferably is from 0.5 to 20 hrs$^{-1}$, more preferably from 3.5 to 12 hrs-1. Preferably from 5 to 100%, more preferably from 8 to 40% of the entire volume of the product mixture is passed by the strongly acidic cation exchange resin and the strongly basic anion exchange resin.

According to step b) of the process of the present invention bisphenol is separated from the product mixture to leave a mother liquor after the product mixture or a portion thereof has optionally been contacted with the strongly acidic cation exchange resin and the strongly basic anion exchange resin.

It is generally known how to separate a produced bisphenol from the product mixture. For the sake of convenience, the generally known reaction step b) will be described in detail in terms of its most preferred embodiments, i.e. in the case of reacting phenol with acetone. When reacting phenol with acetone, the product mixture mainly contains bisphenol A, phenol and by-products, such as 2,2,4-trimethyl-4-(4-hydroxyphenyl)chroman, the o,p'-isomer of bisphenol A, polyphenol and trisphenols. The reaction mixture is advantageously passed to a crystallizer wherein the product mixture is chilled, preferably to a temperature of from 30° to 80° C., more preferably of from 38° to 55° C. The residence time of the product mixture in the crystallizer preferably is from 0.1 to 24 hours, more preferably from 0.5 to 6 hours. Preferably, the product mixture is stirred during the crystallization process. Advantageously, the crystallizer is cooled with water. The major portion of bisphenol A crystallizes out as an adduct with phenol in a 1:1 molar ratio. The bisphenol A/phenol adduct is generally separated from the product mixture in a solid/liquid separation and washing system. Useful solid/liquid separations are for example centrifugation or filtration. The crystals are preferably washed, for example with phenol, a phenolacetone mixture or water, most preferably with phenol alone, to remove mother liquor from the crystals. Preferably, 0.1 to 2.6 parts, more preferably 0.4 to 1.5 parts of phenol are used, based on the weight of bisphenol A/phenol adduct. The separation of the solid bisphenol A/phenol adduct from the product mixture and the washing of the solid adduct is preferably carried out at a temperature of from 35 to 95° C, more preferably of from 38 to 55° C. It has been found that bisphenol A or other bisphenols of very high purity can be produced by washing the solid bisphenol A/phenol adduct or other solid bisphenol products with phenol of which at least a portion has been contacted with a strongly acidic cation exchange resin and a strongly basic anion exchange resin. Preferably from 20 to 100%, more preferably from 50 to 100% and most preferably from 90 to 100% of the volume of phenol which is used for washing the solid bisphenol A/phenol adduct is passed through both indicated types of resins. The treatment can be carried out in the same manner as the treatment of the phenolic starting material which is used as a component of the reaction mixture in step a) of the process described above. Phenol which has been used for washing the solid bisphenol A/phenol adduct is preferably recycled to the reaction mixture. The solid bisphenol A/phenol adduct usually has a residual moisture content (mother liquor and washing liquor) of from 2 to 38%.

Usually the solid bisphenol A/phenol adduct is melted and phenol is recovered by distillation. Recovered phenol may be recycled to the reaction mixture, preferably after having contacted at least a portion of the phenol with a strongly acidic cation exchange resin and a strongly basic anion exchange resin, as described above. The distillation is preferably carried out at a temperature of from 70° to 260° C., more preferably from 150° to 230° C. at a preferred pressure of from 2 to 650 mbar, more preferably from 5 to 180 mbar. The residual molten bisphenol A is generally crystallized, flaked, prilled or granulated. Preferably, the crystallization is carried out in the presence of water, as described in U.S. Pat. Nos. 3,326,986, 4,740,635 and 4,861,919. Bisphenol A can be crystallized from its isomers and excess phenol through the addition of water and heating to a temperature sufficient to melt the crude bisphenol A and other impurities. The molten mass is then cooled to effect the crystallization of bisphenol A, as described in U.S. Pat. No. 3,326,986. Alternatively, bisphenol A can be crystallized from a blend of bisphenol A, diphenol isomers and impurities, the blend being essentially free of phenol, as described in U.S. Pat. No. 4,740,635. Water is added to the blend, the blend is heated to a temperature between 95° and 105° C., and the molten mass is cooled to a temperature below 90° C. As a third alternative, bisphenol A can be purified in a multi-stage counter-current process wherein the crystals are melted by addition of heat and water prior to each crystallization step, as described in U.S. Pat. No. 4,861,919. Solid bisphenol A is separated from a remaining liquid phase. The liquid phase contains water and is optionally recycled to the product mixture.

According to step c) of the process of the present invention at least a portion of the mother liquor which remains after the separation of bisphenol from the product mixture is recycled to the reaction mixture for further usage. The mother liquor mainly contains the phenolic compound, some bisphenol and possibly by-products. The types and amounts of by-products mainly depend on whether the product mixture has passed the mixed bed of ion exchange resins or not. Preferably from 5 to 100%, more preferably from 8 to 40%, most preferably from 10 to 25% of the total volume of the mother liquor is recycled to the reaction mixture. When the product mixture has not been contacted with a strongly acidic cation exchange resin and a strongly basic anion exchange resin, advantageously at least a portion of the mother liquor is contacted with a strongly acidic cation exchange resin and a strongly basic anion exchange resin before mother liquor is recycled to the reaction mixture. The preferred types of strongly acidic cation exchange resin and strongly basic anion exchange resin are the same as the ones described above with reference to the purification of the product mixture. Mother liquor preferably is contacted with a strongly acidic cation exchange resin and a strongly basic anion exchange resin at a temperature of from 40° to 120° C., preferably from 40° to 95° C., more preferably of from 45° to 70° C. The speed of the mother liquor through one or more beds containing said resins, expressed as weight hourly space velocity (WHSV) preferably is from 0.5 to 20 hrs$^{-1}$, more preferably from 3.5 to 12 hrs$^{-1}$. Preferably from 5 to 100%, more preferably from 8 to 80%, most preferably from 10 to 40%, of the entire volume of the mother liquor is passed through a strongly acidic cation exchange resin and strongly basic anion exchange resin. Before mother liquor is contacted with both types of ion exchange resins, it may be subjected to an isomerization process by means of a cation exchanger, such as described in U.S. Pat. Nos. 4,375,567 and 4,882,923.

By passing product mixture or mother liquor through a strongly acidic cation exchange resin and a strongly basic anion exchange resin, a major portion of the impurities contained therein, such as darkly colored materials, organic and/or inorganic acids, such as low molecular weight sulfonic acids originating from the reaction catalyst used in step a) of the process, are efficiently removed. When such impurities were not removed to a sufficient extent, they may cause decomposition of the bisphenol at elevated temperatures due to acid-catalyzed cracking when mother liquor is recycled to the process step a).

By passing at least a portion of the phenolic compound, product mixture and/or mother liquor through a strongly acidic cation exchange resin and a strongly basic anion exchange resin as described above, cracking of the bisphenol and the formation of undesirable compounds can be avoided to a very large extent. Preferably, at least a portion of the mother liquor indicated above and at least a portion, most preferably the entire amount, of the phenolic compound which is used in the process, namely as a component of the reaction mixture in step a) and for washing a solid bisphenol product, such as the solid bisphenol A/phenol adduct, obtained in step b), is contacted with a strongly acidic cation exchange resin and a strongly basic anion exchange resin as described above. The strongly acidic cation and strongly basic anion exchange resins can adsorb or bind impurities, such as organic or inorganic acids, metal moieties, phenol tars, color bodies such as carbonyl, hydroquinone or benzoquinone impurities. Color bodies for example occur when promoters which have been used to promote the catalyst used in step a), such as HS—CH$_2$—CH$_2$—NH$_2$ or (HS—CH$_2$—CH$_2$—)$_2$NH are contacted with iron ions. The number of color bodies can be efficiently decreased by means of the strongly basic anion exchange resin.

The produced bisphenol, such as bisphenol A, has a very high purity and is useful for producing polycarbonate resins. According to the process of the present invention bisphenols, such as bisphenol A, are obtained which generally have a purity of more than 97.5%, usually more than 98% and in most cases even more than 99%. In the case of bisphenol A, the amount of o,p'-isomer generally is less than 1.0%, usually less than 0.7% and in most cases even less than 0.5%, based on the total weight of bisphenol A (including the impurities). The amount of other impurities generally is less than 1.0%, usually less than 0.5% and in most cases even less than 0.3%, based on the total weight of bisphenol A (including the impurities). Bisphenol A produced according to the process of the present invention generally has a color of less 50, typically less than 30 and in most cases even less than 15. The color is determined according to method APHA-ASTM, Test Method D 1209-84 (Reapproved 1988). The lower the figure for the color is, the lighter is the color. Bisphenol A which has been produced for comparative purposes according to the same process, but without treating the product mixture, mother liquor or phenol with a strongly acidic cation exchange resin and a strongly basic anion exchange resin, typically has a purity of 95.1-97.2%, an amount of o,p'-isomer of 1.2-2.2% and an amount of other impurities of 1.7-3.6%, based on the total weight of bisphenol A (including the impurities) and a color of 80-340.

The present invention is further illustrated by the following examples which should not be construed to limit the scope of the present invention. All parts and percentages are by weight.

EXAMPLE 1

In the preparation of bisphenol A 12% of the volume of mother liquor stream which is recycled to the reaction mixture is passed through a column containing a mixed bed of a strongly acidic cation exchange resin and a strongly basic anion exchange resin. The cation exchange resin has a matrix of polystyrene which is cross-linked with 4% divinylbenzene and contains —SO$_3$H groups. The cation exchange resin is commercially available as DOWEX 50WX4 ion exchange resin. The anion exchange resin has a microporous matrix of polystyrene which is cross-linked with on the average 6.5% divinylbenzene. It contains trimethylammonium groups and 80-90% hydroxy groups and 10-20% chloride ions, based on the total number of exchangeable counter-ions. The anion exchange resin is commercially available as DOWEX 550A ion exchange resin. The cation and anion exchange resins are used in a weight ratio of 60% : 40%. The column has a height : diameter ratio of 1.4:1. The mixed bed column is operated at a temperature of 55°-59° C. The velocity (WHSV) of the mother liquor stream through the column is 8.6 hrs$^{-1}$. Two samples of mother liquor are analyzed. The first, comparative sample of mother liquor is extracted before the mixed bed column is installed in the bisphenol A production process. The second sample of mother liquor is extracted after the mixed bed column has continuously been operated for 7 days. 2000 g of each sample are distilled at 200° C. and at an absolute pressure of 10 mbar for 6 hours in order to determine the tendency of the samples to decompose. Both samples are analyzed before and after distillation by gas chromatography to determine the components. The percentage of cracked compounds due to distillation and the color of the mother liquor and the produced bisphenol A, measured according to APHA-ASTM No. D 1209 are listed in the following table I.

TABLE I

| Trial No. | untreated mother liquor and phenol | | mother liquor passed through mixed bed | | bisphenol A end product (mother liquor treated). |
|---|---|---|---|---|---|
| | % cracking | color | % cracking | color | color |
| 1 | 17.2 | 275 | 0 | 75 | 6 |
| 2 | 15.8 | 260 | 0 | 85 | 5 |

EXAMPLE 2

6% of the volume of mother liquor stream which is recycled to the reaction mixture and the entire amount of phenol which is used in the bisphenol A production process is each passed through a column containing a mixed bed of a strongly acidic cation and a strongly basic anion exchange resin as described in Example 1. A portion of the phenol and mother liquor which have been treated in such a manner is used for washing the solid bisphenol A/phenol adduct in a ratio of 0.55 weight parts washing liquor per weight part of solid adduct. After the mixed bed has continuously been operated for seven days in the same manner as in Example 1, samples are extracted and distilled in the same way as in Example 1. The percentage of cracked compounds due to distillation and the color of the mother liquor and of the produced bisphenol A, measured according to APHA-ASTM No. 1209 are listed in the following table II.

TABLE II

| Trial No. | untreated mother liquor and phenol | | mother liquor and phenol passed through mixed bed | | bisphenol A end product (mother liquor and phenol treated) |
|---|---|---|---|---|---|
| | % cracking | color | % cracking | color | color |
| 1 | 16.5 | 280 | 0 | 60 | 3 |
| 2 | 15.6 | 270 | 0 | 65 | 2 |

EXAMPLE 3

The entire amount of phenol which is used in the bisphenol A production process is passed through two columns. The first column contains the strongly acidic cation resin described in Example 1, which is commercially available as DOWEX 50WX4 ion exchange resin. The second column contains the strongly basic anion exchange resin described in Example 1, which is commercially available as DOWEX 550A ion exchange resin. The velocity (WHSV) of the phenol through both columns is 4.3 hrs$^{-1}$. The columns are operated at a temperature of 55°-59° C. A portion of the phenol which has been treated in such a manner is used for washing the solid bisphenol A/phenol adduct in a ratio of 0.55 weight parts washing liquor per weight part of solid adduct. After the two columns have continuously been operated for seven days, samples are extracted and distilled in the same way as in Example 1. The percentage of cracked compounds due to distillation and the color of the mother liquor and of the produced bisphenol A, measured according to APHA-ASTM No.D-1209 are listed in the following table III.

TABLE III

| Trial No. | untreated mother liquor and phenol | | Phenol passed through mixed bed | | bisphenol A end product (phenol treated) |
|---|---|---|---|---|---|
| | % cracking | color | % cracking | color | color |
| 1 | 15.9 | 285 | 0.11 | 140 | 11 |
| 2 | 15.6 | 290 | 0.12 | 125 | 9 |

A comparison between Tables I, II and III illustrates that better results are achieved when a strongly acidic cation exchange resin and a strongly basic anion exchange resin is utilized to purify mother liquor and phenol, when compared to the purification of mother liquor only or of phenol only.

EXAMPLE 4 AND COMPARATIVE EXAMPLES

The efficiency of purifying a mother liquor stream in the described bisphenol A production process is tested by passing the mother liquor through a) a mixed bed containing 60 weight% of a strongly acidic cation resin which is commercially available as DOWEX 50WX4 ion exchange resin and 40 weight% of a strongly basic anion exchange resin which is commercially available as DOWEX 550A ion exchange resin (according to the present invention) or b) a strongly acidic cation resin which is commercially available as DOWEX 50WX4 ion exchange resin (as generally suggested in U.S. Pat. Nos. 4,354,045 and 4,107,218) or c) a strongly basic anion exchange resin which is commercially available as DOWEX 550A ion exchange resin (as generally suggested in U.S. Pat. No. 4,766,254) or d) a first column containing a strongly acidic cation resin which is commercially available as DOWEX 50WX4 ion exchange resin and then through a second column containing a macroporous weakly basic anion exchange resin which is commercially available as DOWEX AMW 500 UG ion exchange resin (as generally suggested in U.S. Pat. No. 4,191,843). The weekly basic anion exchange resin has a matrix of polystyrene which is cross-linked with 8% divinylbenzene and contains dimethylamine groups.

Four equal samples of mother liquor are passed through the ion exchange resins a), b) c) or d) at a temperature of 55° C. and a velocity (WHSV) of 8.6 hrs$^{-1}$. 2000 g of each sample, after having passed through the ion exchange resins a), b) c) or d), are distilled in a glass equipment during 6 hours at 190° C. and a pressure of 10 mbar. For comparative purposes 4 samples of mother liquor which have not been passed through an ion exchange resin bed are distilled in the same manner. All eight samples are analyzed before and after distillation by gas chromatography to determine the compounds.

The entire trial is once repeated. The percentage of cracked compounds due to distillation are listed in the following table IV.

TABLE IV

| ion exchange resin treatment (trial no.) | % cracking | |
|---|---|---|
| | before treatment | after treatment |
| a(1) | 27.8 | 0.01 |
| a(2) | 29.4 | 0.01 |
| b(1) | 26.4 | 9.21 |
| b(2) | 28.7 | 8.26 |
| c(1) | 28.3 | 0.80 |
| c(2) | 26.9 | 0.72 |
| d(1) | 27.3 | 4.71 |
| d(2) | 30.2 | 4.54 |

Table IV illustrates the substantial and surprising improvement of the process of the present invention as compared to the methods generally suggested by the prior art. The much lower percentage of cracking after the treatment according to examples a(1) and a(2), as compared to comparative runs b), c), and d), indicates that the mother liquor contains a considerably lower amount of undesirable by-products which facilitate cracking of the compounds in the mother liquor.

What is claimed is:

1. A process of preparing a bisphenol comprising the steps of:
   a) reacting a phenolic compound selected from the group consisting of phenol, cresols, xylenols, chlorophenols, thymol, carvacrol, cumenol, 2-methyl-6-ethylphenol, 2,4-dimethyl-3-ethylphenol, 4-ethylphenol, 2-ethyl-4-methylphenol, 2,3,6-trimethylphenol, 2-methyl-4-tertiary-butylphenol, 2,4-ditertiary-butyl-phenol, 4-methyl-2-tertiary-butylphenol, 2-teritary-butyl-4-methylphenol, 2,3,5,6-tetramethylphenol, 2,6-dimethylphenol, 2,6-ditertiary-butylphenol, 3,5-dimethylphenol, 3,5-diethylphenol, 2-methyl-3,5-diethylphenol, o-phenylphenol, p-phenylphenol, tetraphenolethane, the naphthols and phenanthrol with a carbonyl compound having the formula:

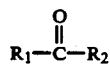

wherein $R_1$ is selected from the group consisting of aliphatic, cycloaliphatic and aromatic radicals, and $R_2$ is selected from the group consisting of aliphatic, cycloaliphatic, aromatic radicals and hydrogen in a reaction mixture, containing said carbonyl compound, a stoichiometric excess of said phenolic compound and a strongly acidic ion exchange resin catalyst, to produce a product mixture containing a bisphenol;
   b) separating bisphenol from the product mixture to leave a motor liquor; and
   c) recycling at least a portion of the mother liquor to the reaction mixture,
wherein at least one of the following steps is conducted:
   i) at least a portion of the phenolic compound is contacted with a strongly acidic cation exchange resin and a strongly basic anion exchange resin before the phenolic compound is used in reaction step a);
   ii) at least a portion of the product mixture is contacted with a strongly acidic cation exchange resin and a strongly basic anion exchange resin before mother liquor is recycled to the reaction mixture; or
   iii) at least a portion of the mother liquor is contacted with a strongly acidic cation exchange resin and a strongly basic anion exchange resin before mother liquor is recycled to the reaction mixture.

2. The process of claim 1, wherein at least a portion of both the phenolic compound and the mother liquor is contacted with a strongly acidic cation exchange resin and a strongly basic anion exchange resin.

3. The process of claim 1, wherein the strongly acidic cation exchange resin and the strongly basic anion exchange resin are arranged in a mixed bed.

4. The process of claim 2, wherein the strongly acidic cation exchange resin and the strongly basic anion exchange resin are arranged in a mixed bed.

5. The process of claim 3, wherein the mixed bed contains from 50 to 70 weight percent of the strongly acidic cation exchange resin, based on the total of the cation and anion exchange resin.

6. The process of claim 4, wherein the mixed bed contains from 50 to 70 weight percent of the strongly acidic cation exchange resin, based on the total of the cation and anion exchange resin.

7. The process of claim 1 wherein the strongly acidic cation exchange resin contains —$SO_3H$ groups.

8. The process of claim 1 wherein the strongly basic anion exchange resin contains —$NR_3R_4R_5OH$ groups wherein $R_3$ and $R_4$ are, each independently, hydrogen or $C_{1-6}$-alkyl, and $R_5$ is hydrogen, $C_{1-6}$-alkyl, hydroxy-$C_{1-3}$-alkyl or a mono- or di-$C_{1-6}$-alkylaminoethylene group.

9. The process of claim 1 wherein the strongly acidic cation exchange resin contains a matrix of a cross-linked polystyrene or a cross-linked poly(alpha-methylstyrene) or a cross-linked polymer of styrene or alpha-methylstyrene which is substituted at the benzene ring with $C_{1-6}$-alkyl or halogeno-$C_{1-6}$-alkyl and the resin is in the form of beads which have a decreased level of cross-linkages in the shell area as compared to the core area.

10. The process of claim 1 wherein the strongly basic anion exchange resin contains a matrix of a cross-linked polystyrene or a cross-linked poly(alpha-methylstyrene) or a cross-linked polymer of styrene or alpha-methylstyrene which is substituted at the benzene ring with $C_{1-6}$-alkyl or halogeno-$C_{1-6}$-alkyl and the resin is in the form of beads which have a decreased level of cross-linkages in the shell area as compared to the core area.

11. The process of claim 1 wherein at least one member of the group consisting of product mixture, mother liquor and phenolic compound is contacted with the strongly acidic cation exchange resin and the strongly basic anion exchange resin at a temperature of form about 40° to about 95° C.

12. The process of claim 1 wherein water and carbonyl compound are removed from the product mixture before bisphenol is separated from the product mixture.

13. The process of claim 1 wherein the carbonyl compound is selected from the group consisting of acetone, 1,3-dichloroacetone, dimethyl ketone, methyl ethyl ketone, diethyl ketone, dibutyl ketone, methyl isobutyl ketone, cyclohexanone, fluoroenone, propionylphenone, methyl amyl ketone, mesityl oxide, cyclopentanone, acetophenone, formaldehyde, acetaldehyde, propionaldehyde, butyraldehyde and benzaldehyde.

14. The process of claim 1 wherein the carbonyl compound is acetone or fluorenone.

15. The process of claim 1 wherein phenol is reacted with acetone to produce bisphenol A.

16. The process of claim 15 wherein bisphenol A is separated from the product mixture in the form of a bisphenol A/phenol adduct.

17. The process of claim 16 wherein bisphenol A/phenol adduct is washed with phenol which has been contacted with a strongly acidic cation exchange resin and a strongly basic anion exchange resin.

18. A bisphenol produced according to the process of claim 1.

19. Bisphenol A produced according to the process of claim 16.

* * * * *